(12) United States Patent
Salomir et al.

(10) Patent No.: US 8,317,731 B2
(45) Date of Patent: Nov. 27, 2012

(54) METHOD AND GEL COMPOSITION TO PREVENT REFLECTION OF HIFU AT TISSUE-AIR INTERFACE

(75) Inventors: Rares Salomir, Ambilly (FR); Magalie Viallon, Lyons (FR)

(73) Assignee: Siemens Aktiegesellschaft, Munich (DE)

(*) Notice: Subject to any disclaimer, the term of this patent is extended or adjusted under 35 U.S.C. 154(b) by 194 days.

(21) Appl. No.: 12/835,996

(22) Filed: Jul. 14, 2010

(65) Prior Publication Data

US 2012/0016271 A1 Jan. 19, 2012

(51) Int. Cl.
*A61H 1/00* (2006.01)
(52) U.S. Cl. ............................................................. 601/2
(58) Field of Classification Search ... 601/2; 252/408.1; 600/439
See application file for complete search history.

(56) References Cited

U.S. PATENT DOCUMENTS 6,508,774 B1 * 1/2003 Acker et al. ...................... 601/2

* cited by examiner

*Primary Examiner* — Michael Rozanski
(74) *Attorney, Agent, or Firm* — Schiff Hardin LLP

(57) ABSTRACT

In order to reduce reflection and heating of a high intensity focused ultrasound (HIFU) beam following a region of interest in tissue to which an HIFU beam was administered, at least two layers of aquasonic gel are applied at a tissue/air interface following the region of interest and the focus in a direction of propagation of the HIFU beam. A first of the two aquasonic gel layers is a foamed aquasonic gel layer, and a second of the two layers is substantially bubble-free aquasonic gel. The layer of foamed aquasonic gel is placed directly adjacent the tissue/air interface, and the layer of substantially bubble-free aquasonic gel is placed over the layer of foamed aquasonic gel, at a side thereof facing away from the tissue/air interface.

6 Claims, 2 Drawing Sheets

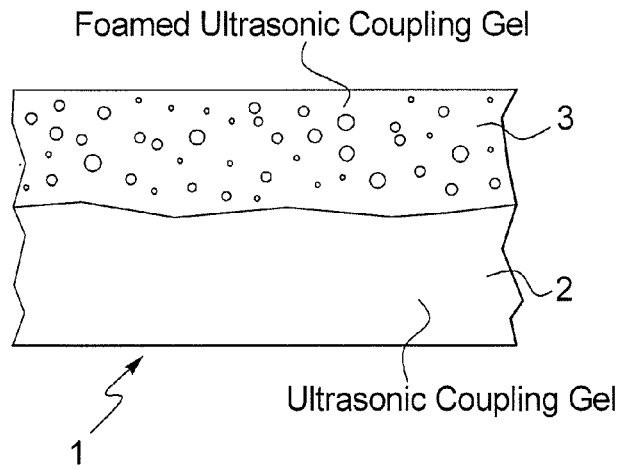
*FIG. 1*
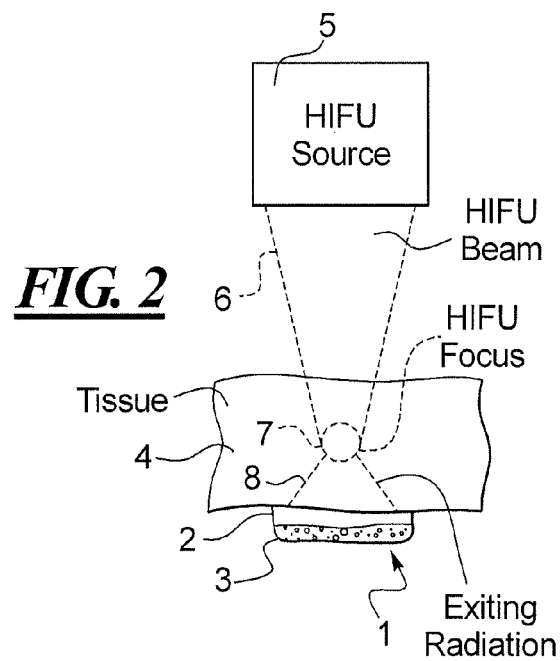
*FIG. 2*
*FIG. 3*
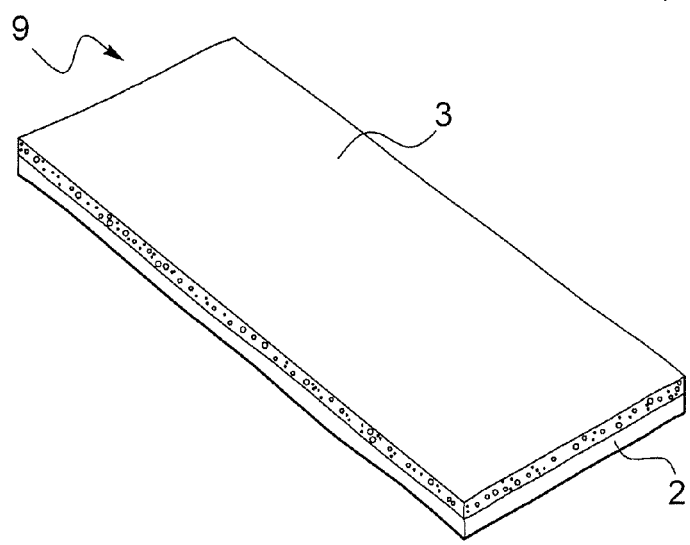

US 8,317,731 B2

METHOD AND GEL COMPOSITION TO PREVENT REFLECTION OF HIFU AT TISSUE-AIR INTERFACE

BACKGROUND OF THE INVENTION

1. Field of the Invention

The present invention is concerned with protection against high intensity focused ultrasound (HIFU) reflection and far field heating.

2. Description of the Prior Art

Magnetic resonance guided high intensity focused ultrasound (MRg HIFU) is a hybrid technology that offers efficient and safe thermal ablation of targeted tumors or other pathological tissues, while preserving the healthy surrounding structures. Theoretically, MRgHIFU has no limitation as to the size of the lesion that can be treated. The primary challenge is to avoid near and far field heating that occur due to the continued passage of HIFU through tissue after the region of interest has been irradiated. Particularly at the patient body location at which the radiation exits the patient's body, reflection and heating can occur due to the tissue/air interface at that location. This location is typically approximately opposite the entry point of HIFU into the patient's body, with the region of interest being between the entry location and the exit location.

SUMMARY OF THE INVENTION

It is an object of the present invention to reduce reflection and far field heating that occur in a HIFU procedure.

This object is achieved in accordance with the present invention by a method that includes applying multi-layer ultrasonic coupling gel to the patient at the exit location of HIFU with which a region of interest in the patient has been irradiated. The multi-layer ultrasonic coupling gel is composed of a minimum of two layers. A first layer, which is located directly adjacent to the patient's skin, is composed of commercial ultrasonic coupling gel in untreated form, i.e., homogeneous, with substantially no gas bubbles therein. A second layer, that is directly adjacent the side of the bubble-containing gel layer facing away from the patient, is composed of commercially available ultrasonic coupling gel that has been whipped or beaten in order to introduce air bubbles therein, so that the air bubbles are randomly dispersed and suspended within the gel ultrasonic coupling The multi-layer gel can be applied topically, with a layer of the non-foamed gel being applied directly to the patient's skin, followed by application of a layer of the foamed gel on top of the non-foamed gel.

The invention also encompasses a pre-formed gel product, such as a sheet, that is composed of a layer of foamed aquasonic gel and a directly adjacent layer of non-foamed aquasonic gel. The sheet can be rectangular and can then be cut to any desired shape in order to conform to the contours of particular body regions, or can be pre-formed in multiple different shapes.

DESCRIPTION OF THE DRAWINGS

FIG. 1 is a side view of a portion of a multi-layer aquasonic gel composition in accordance with the present invention.

FIG. 2 schematically illustrates the use of the multi-layer gel composition shown in FIG. 1 in a HIFU procedure.

FIG. 3 is a perspective view of an embodiment of a multi-layer gel product in accordance with the present invention.

DESCRIPTION OF THE PREFERRED EMBODIMENTS

Figure 4:
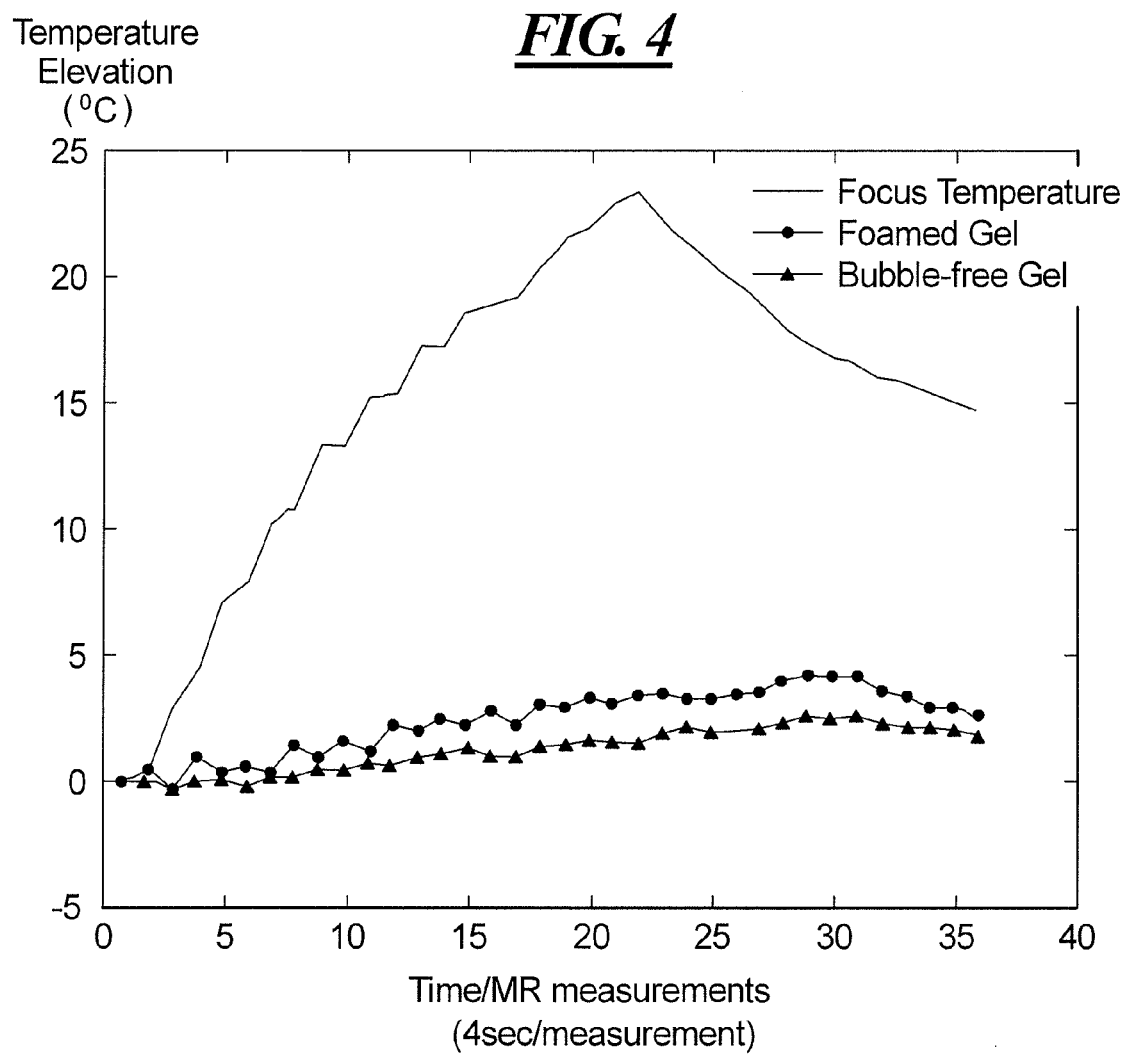
FIG. 4 is a graph showing temperature measurements for explaining the effectiveness of the inventive method and gel composition.

FIG. 1 is a side view of an embodiment of a gel composition in accordance with the present invention. The gel composition 1 is, in this embodiment, composed of a layer 2 of commercially available aquasonic gel in basically untreated form, and a layer 3 of foamed aquasonic gel that has been beaten or whipped so as to introduce bubbles therein. The bubbles are randomly dispersed within the layer 3, and are suspended within the aquasonic gel in that layer. The aquasonic gel in the layer 2, by contrast, is as free of bubbles as possible.

The foamed aquasonic gel in the layer 3 can be produced by any suitable manner, such as by using beaters to whip or beat an amount of commercially available aquasonic gel.

The bubbles are distributed substantially uniformly in the layer 3.

An example of a commercially available aquasonic gel that is suitable for use as the layer 2, and to produce the layer 3, is Aquasonic® 100.

FIG. 2 schematically illustrates the use of the gel composition 1 in a HIFU procedure. The composition 1 is either topically applied by spreading on the patient's skin, or applied in the form of a ready-made product 9 as shown in FIG. 3. The non-foamed aquasonic gel layer 2 is directly adjacent the patient's skin, as shown in FIG. 2.

In a HIFU procedure, a HIFU source 5 is operated to produce a HIFU beam 6 that is focused to a HIFU focus. The HIFU source 5 is positioned and oriented, such as by using magnetic resonance guidance, so that the HIFU focus substantially coincides with a region of interest 7 within tissue of the patient, that is to be treated with HIFU. The HIFU beam 6 is thus radiated into the tissue in a propagation direction. After the region of interest 7 in the propagation direction, HIFU will continue to propagate through the tissue, as radiation 8, which will not necessarily remain as precisely focused as preceding the region of interest 7. Therefore, this radiation 8 is generally described as scatter radiation in FIG. 2, the term "scatter" being synonymous with "dispersed."

As a result of the radiation 8 exiting the patient at the tissue/air (skin/air) interface, reflection and localized heating of the tissue occur, which can be uncomfortable for the patient and, if severe, could cause injury. By placing the gel composition 1 on the patient's skin so as to substantially cover the exit region, the beam will freely exit the patient or tissue and propagate in the non-foamed layer 2, finally entering layer 3 while multiple reflections in the foam will scatter the residual beam, so the layer 3 plays the role of an absorber. The relevant mechanism appears to be that, when the HIFU beam encounters the non-foamed layer 2, it proceeds therethrough with substantially no deflection or absorption occurring, and the beam then encounters the foamed layer 3. In the foamed layer 3, the remaining HIFU beam (beam energy) substantially vanishes, presumably due to multiple reflections produced by the bubbles in the foam. The lattice of bubbles is presumed to randomly split the HIFU beam by sequential reflections/deflections, so as to distribute the remaining energy of the HIFU beam in the gel in the layer 3.

FIG. 4 shows magnetic resonance thermometry (PRFS method) time curves obtained in a region of interest positioned in the layer 3 (curve indicated by circles), and in the layer 2 (curve indicated by triangles), and in tissue (continuous curve). As can be seen from FIG. 4, the tissue being treated with HIFU reached a temperature elevation of 23.5° C. at the focus, whereas a maximum temperature of 3° C. occurred in the layer 2 and a maximum temperature of 4.5° C. occurred in the foamed layer 3.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for reducing reflection and tissue heating in a high intensity focused ultrasound (HIFU) procedure, comprising the steps of:

identifying a location of a patient at which HIFU, administered at a HIFU focus, encounters a tissue/air interface in a propagation direction after said HIFU focus;

covering said location, immediately adjacent said tissue/air interface, with a first layer of ultrasonic coupling gel, said first layer consisting of substantially bubble-free ultrasonic coupling gel;

covering said location with a second layer of ultrasonic coupling gel, overlying said first layer of ultrasonic coupling gel at a side of said first layer of ultrasonic coupling gel opposite said tissue/air interface, said second layer consisting of foamed ultrasonic coupling gel.

2. A method as claimed in claim 1 comprising topically applying said first layer as flowable ultrasonic coupling gel at said tissue/air interface, and topically applying said second layer, as flowable ultrasonic coupling gel, on the topically applied first layer.

3. A method as claimed in claim 1 comprising simultaneously applying said first and second layers as a pre-formed sheet comprising said first layer and said second layer.

4. A method for conducting a high intensity focused ultrasound (HIFU) procedure, comprising the steps of:

administering HIFU to a region of interest in tissue of a subject by introducing a HIFU beam into the tissue, said beam having a beam focus that substantially coincides with a region of interest in the tissue;

at a tissue/air interface of said beam following said region of interest and said focus in a direction of propagation of said beam, applying a first gel layer consisting of substantially bubble-free ultrasonic coupling gel immediately adjacent said tissue/air interface, and applying a second gel layer consisting of foamed ultrasonic coupling gel over said layer of substantially bubble-free ultrasonic coupling gel at a side of said layer of substantially bubble-free ultrasonic coupling gel facing away from said tissue/air interface.

5. A method as claimed in claim 4 comprising topically applying said first gel layer as flowable gel at said tissue/air interface, and topically applying said second gel layer, as flowable gel, on the topically applied first layer.

6. A method as claimed in claim 4 comprising simultaneously applying said first and second gel layers as a pre-formed sheet comprising said first gel layer and said second gel layer.

\* \* \* \* \*